United States Patent
Durbin et al.

(10) Patent No.: US 7,328,077 B2
(45) Date of Patent: *Feb. 5, 2008

(54) METHOD AND SYSTEM FOR AUTOMATED MASS MANUFACTURING OF CUSTOM TOOTH DIE MODELS FOR USE IN THE FABRICATION OF DENTAL PROSTHETICS

(76) Inventors: Duane Milford Durbin, 7660 Norcanyon Way, San Diego, CA (US) 92126; Dennis Arthur Durbin, 711 Marsolan, Solana Beach, CA (US) 92075

( * ) Notice: Subject to any disclaimer, the term of this patent is extended or adjusted under 35 U.S.C. 154(b) by 480 days.

This patent is subject to a terminal disclaimer.

(21) Appl. No.: 11/104,999

(22) Filed: Apr. 13, 2005

(65) Prior Publication Data

US 2005/0177261 A1  Aug. 11, 2005

Related U.S. Application Data

(63) Continuation-in-part of application No. 10/336,163, filed on Jan. 6, 2003, now Pat. No. 6,882,894.

(51) Int. Cl.
*G06F 19/00* (2006.01)
(52) U.S. Cl. .................. 700/98; 700/118; 433/213
(58) Field of Classification Search ............ 700/96, 700/98, 118–120, 182; 264/19; 433/213
See application file for complete search history.

(56) References Cited

U.S. PATENT DOCUMENTS

| | | | |
|---|---|---|---|
| 4,324,546 A | 4/1982 | Heitlinger et al. | |
| 4,575,805 A | 3/1986 | Moermann et al. | |
| 4,611,288 A | 9/1986 | Duret et al. | |
| 4,793,806 A | 12/1988 | Elledge | |
| 4,937,928 A | 7/1990 | Van der Zel | |
| 5,257,203 A | 10/1993 | Riley et al. | |
| 5,378,154 A * | 1/1995 | Van Der Zel | ............... 433/223 |
| 5,452,219 A | 9/1995 | Dehoff et al. | |
| 5,587,912 A | 12/1996 | Andersson et al. | |
| 5,798,924 A | 8/1998 | Eufinger et al. | |
| 5,823,778 A | 10/1998 | Schmitt et al. | |
| 5,975,893 A | 11/1999 | Chishti et al. | |
| 6,174,168 B1 * | 1/2001 | Dehoff et al. | ............ 433/202.1 |
| 6,210,162 B1 | 4/2001 | Chishti et al. | |
| 6,227,850 B1 | 5/2001 | Chishti et al. | |
| 6,364,660 B1 | 4/2002 | Durbin et al. | |
| 6,386,867 B1 | 5/2002 | Durbin et al. | |
| 6,386,878 B1 | 5/2002 | Pavlovskaia et al. | |
| 6,478,580 B1 | 11/2002 | Silva | |
| 6,554,613 B1 | 4/2003 | Sachdeva et al. | |
| 6,688,886 B2 | 2/2004 | Hughes et al. | |
| 6,882,894 B2 | 4/2005 | Durbin et al. | |
| 2003/0222366 A1 | 12/2003 | Stangel et al. | |
| 2003/0224312 A1 | 12/2003 | Bergersen | |

* cited by examiner

*Primary Examiner*—Zoila Cabrera

(57) ABSTRACT

Methods and systems for treating teeth include capturing a digital dental model taken within an oral cavity; modifying the digital model in planning a dental treatment or in designing a tooth die model for a dental prosthetic; creating physical models from the original or modified digital models: and using the physical models as a pattern for fabrication and fit check of a dental prosthetic.

17 Claims, 5 Drawing Sheets

METHOD AND SYSTEM FOR AUTOMATED MASS MANUFACTURING OF CUSTOM TOOTH DIE MODELS FOR USE IN THE FABRICATION OF DENTAL PROSTHETICS

This application is a continuation in part of application Ser. No. 10/336,163 filed on Jan. 6, 2003, now U.S. Pat. No. 6,882,894, the content of which is incorporated by reference.

BACKGROUND

The present invention relates to utilizing digital dental models to directly manufacture custom tooth die models that can be used as a pattern to fabricate dental prosthetics such as crowns.

In many dental applications, a physical model of a patient's teeth is needed that faithfully reproduces the patient's teeth and other dental structures, including the jaw structure. Conventionally, a three-dimensional negative model of the teeth and other dental structures is created during an impression-taking session where one or more trays are filled with a dental impression material and the tray is then placed over the teeth to create a negative mold. Once the impression material has hardened, the tray of material is removed from the teeth and a plaster like material is poured into the negative mold formed by the impression. After hardening, the poured plaster material is removed from the impression mold and, as necessary, finish work is performed on the casting to create the final physical model of the dental structure. Typically a physical model will include at least one tooth and the adjacent region of gingiva. Physical models may also include all of the teeth of a jaw, the adjacent gingiva and, for the upper jaw, the contour of the palate.

Dental laboratories typically use the physical model as a pattern for the fabrication and fitting of a variety of precision fitted dental prosthetic devices such as crowns, bridges, retainers and veneers. Often, the technician performs a significant amount of work on the physical model to prepare it for use as the pattern for the dental fabrication. For example, when a single tooth crown is to be made, the technician will perform a number of operations to isolate and remove the tooth of interest from the model. First the bottom of the model will be ground flat. The technician will then drill a hole and install a coated pin at the bottom of the tooth model (die) of interest. The pin provides a means of handling the isolated tooth die during the subsequent steps involved in the crown being fabricated. The pinned model is then placed on the top of a base mold tray that has been filled with unhardened plaster material. After the material hardens, the model is now attached to the base form with the coated pin embedded in the base mold. The technician then makes two vertical cuts on each side of the pinned tooth model being careful not to cut or remove material from the tooth model of interest or the adjacent teeth of the model. Because the pin was coated, the plaster material does not adhere to the pin and the cutout tooth die can now be removed from the model/base assembly. The pinned tooth die can now be used as the model to fabricate the crown.

Typically, once the crown has been fabricated, the crown will be installed on the tooth die and placed back on the model/base assembly to verify the fit of the crown with the adjacent teeth in the model. As can be appreciated, the process of cutting the tooth of interest out of the model/base assembly creates the opportunity to damage either the tooth of interest or the adjacent teeth in the model, which results in a potentially poor fitting crown in the patient.

Automated dental structure scanning techniques have been developed as alternatives to the mold casting procedure. Because these techniques can create a direct digital representation of the dental structures, they provide the advantage of creating an "electronic impression" that is immediately transmittable from the patient to a dental Computer Aided Design (CAD) system and, after review and annotation by a dentist, to a dental laboratory. The digital transmission potentially diminishes inconvenience for the patient and eliminates the risk of damage to the impression mold.

For example, U.S. Pat. No. 6,364,660 discloses a method and apparatus for mapping the structure and topography of dental formations such as peridontium and teeth, both intact and prepared, for diagnosis and dental prosthetics and bridgework by using an intra-oral image scanning technique. As claimed therein, the method can provide a digital 3D model that captures details of orally situated dental formations thus enabling diagnosis and the preparation of precision moldings and fabrications that will provide greater comfort and longer wear to the dental patient.

In parallel with the advancement in the methods and means to create digital dental models, computer aided design (CAD) systems have been developed for use by dental practitioners, which utilize these digital models. Typically, these systems allow the user to view, shift and rotate the digital model as well as perform a variety of measurements. In addition, these CAD systems can transfer files and be interfaced to Computer Integrated Manufacturing (CIM) equipment, such as a CNC milling machine, to fabricate a physical dental model or prosthetic from the digital model file. These CAD systems however do not provide the features needed by dental laboratories to eliminate the manual steps required to create a tooth die.

SUMMARY

In one aspect, a method for using a digital dental model; allowing authorized users to specify the dental area of interest; isolating the specified dental area of interest from the original digital dental model; creating a new 3D digital model file for the isolated tooth area of interest; creating a digital isolated tooth die model by appending to the isolated tooth 3D digital model file either 1) a 3D digital model file of a base with a mounting post or stem, or 2) a base with a hole sized to receive a pre-fabricated mounting post or stem, with such mounting post, stem or hole dimensioned to the base of the isolated dental area; creating physical models of both the original digital dental model and the digital isolated tooth die model; and archiving the digital models.

Implementations of the above aspect may include one or more of the following. A dental Computer Aided Design (CAD) system can be used to view the digital dental model and select the teeth that need to be isolated. The dental CAD system can then create 3D digital isolated tooth die models for each of the selected teeth. A Computer Integrated Manufacturing (CIM) system can create physical models representative of the original digital dental model and the digital isolated tooth die models.

Other aspects of the present invention are described in the following detailed description of the invention, in the claims and in the accompanying drawings.

DESCRIPTION

Figure 1:
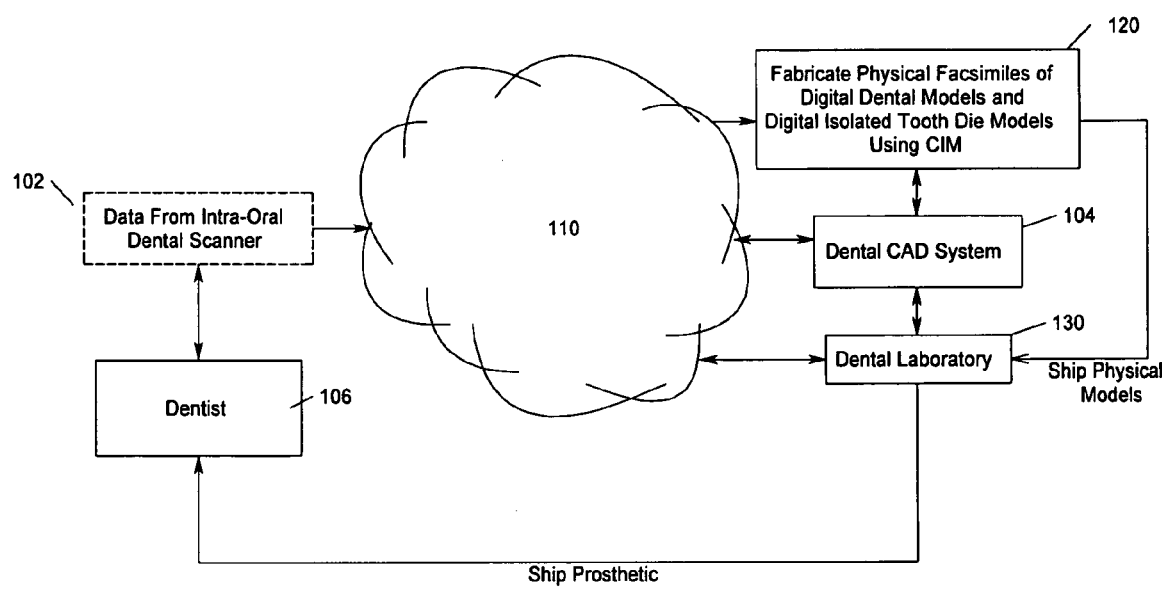
FIG. 1 is a block diagram illustrating an exemplary environment for viewing, altering, and archiving digital models of dental structures and for supporting computer integrated manufacturing of physical models of the dental structures using the digital model files.

FIG. 1 is a block diagram that illustrates an exemplary environment for viewing, altering, and archiving digital models of dental structures and for supporting computer integrated manufacturing of physical models of the dental structures using the digital model files. In the environment of FIG. 1, data obtained by an intra-oral scanner 102 of the dental structures is used to create a 3D digital dental model that is representative of the surface contour of the scanned dental structures. Descriptions of the method and apparatus to obtain this digital dental model are described in U.S. Pat. No. 6,364,660, the contents of which are incorporated by reference herein.

The data representing the digital dental model from the scanner 102 is transferred over a wide area network 110 such as the Internet to a dental laboratory facility 130 with computer aided manufacturing capabilities. Using the Dental CAD System 104 a dental laboratory technician may view the digital dental model and select those teeth for which a tooth die model is desired. The Dental CAD System 104 would then create 3D digital isolated tooth die models of the selected teeth. The technician could then select which of the digital models should be fabricated into a physical model utilizing CIM methods and technologies such as Stereo Lithography Apparatus (SLA). Typically, a CIM fabricated isolated tooth die model would be used as a pattern to fabricate a prosthetic such as a crown that would then be shipped directly back to the dentist 106.

In some cases, the dentist 106 may transfer the digital dental model file to a CIM facility 120. The CIM facility 120 may choose to make dentist-sanctioned modifications to the digital dental model and then fabricate the physical replicates of the digital dental model and the digital isolated tooth die model following the processes described previously for the dental laboratory 130. Once the physical models of the digital dental model and the digital isolated tooth die model are made, the physical models would be shipped to the requested dental laboratory 130 for prosthetic fabrication.

The system of FIG. 1 integrates the creation of digital dental models with CIM to fabricate accurate physical model representations of the digital models. The invention addresses the CIM of physical models ranging from an individual isolated tooth die model to a dental model comprised of all of the teeth in a jaw. The CIM technologies that are suitable for fabrication of physical models of the digital models includes, but is not limited to stereo lithography apparatus (SLA), computer numeric controlled (CNC) machining, electro-discharge machining (EDM), and Swiss Automatics machining. For example, SLA equipment and 3D printers such as the ThermoJet printer are available from 3D Systems, Inc. of Valencia, Calif. that allows CAD users the freedom to quickly "print" and hold a 3-dimensional model in their hands.

In stereolithography, three-dimensional shape model data is converted into contour line data and sectional shapes at respective contour lines are sequentially laminated to prepare a cubic model. Each cubic ultraviolet-ray curable resin layer of the model is cured under irradiation of a laser beam before the next layer is deposited and cured. Each layer is in essence a thin cross-section of the desired three-dimensional object. Typically, a thin layer of viscous curable plastic liquid is applied to a surface which may be a previously cured layer and, after sufficient time has elapsed for the thin layer of polymerizable liquid to smooth out by gravity, a computer controlled beam of radiation is moved across the thin liquid layer to sufficiently cure the plastic liquid so that subsequent layers can be applied thereto.

The waiting period for the thin layer to level varies depending on several factors such as the viscosity of the polymerizable liquid, the layer thickness, part geometry, and cross-section, and the like. Typically, the cured layer, which is supported on a vertically movable object support platform, is dipped below the surface of a bath of the viscous polymerizable liquid a distance greater than the desired layer thickness so that liquid flows over the previous cross-section rapidly. Then, the part is raised to a position below the surface of the liquid equal to the desired layer thickness, which forms a bulge of excess material over at least a substantial portion of the previous cross-section. When the surface levels (smooth out), the layer is ready for curing by radiation. An ultraviolet laser generates a small intense spot of UV which is moved across the liquid surface with a galvanometer mirror X-Y scanner in a predetermined pattern. In the above manner, stereolithography equipment automatically builds complex three-dimensional parts by successively curing a plurality of thin layers of a curable medium on top of each other until all of the thin layers are joined together to form a whole part such as a dental model.

As can be appreciated, each patient's dental model is unique and a patient's dental models are typically manufactured one at a time by a skilled dental technician. In contrast to this "one-at-a-time" manual fabrication of models, the use of SLA allows for the mass manufacturing of patient dental models since the platform can be sectioned into grids where each grid can support a unique set of dental model parts. In addition, these unique grid model parts can be serialized during manufacturing to allow tracking of individual parts throughout the dental laboratory process.

For a typical single tooth crown patient, three unique physical models would be made: 1) A physical model of all or part of the teeth and adjacent gingiva in the digital dental model derived from scanning the dental structures in the upper jaw; 2) A physical model of all or part of the teeth and adjacent gingiva in the digital dental model derived from scanning the dental structures in the lower jaw; and 3) A physical model of the digital isolated tooth die model for the tooth being crowned. The upper and lower jaw physical models would be fabricated with index marks allowing the lab technician or dentist to align the physical models in the proper occlusal relationship. Once the dental technician has fabricated the crown using the physical model of the digital isolated tooth die model as a pattern, the crown can be checked for fit by seating it on the corresponding tooth location of the physical model created from the digital dental model for the upper or lower jaw. This allows for an accurate check of both adjacent tooth interference and occlusal fit of the fabricated crown prosthetic prior to shipping the crown prosthetic to the dentist.

Figure 2:
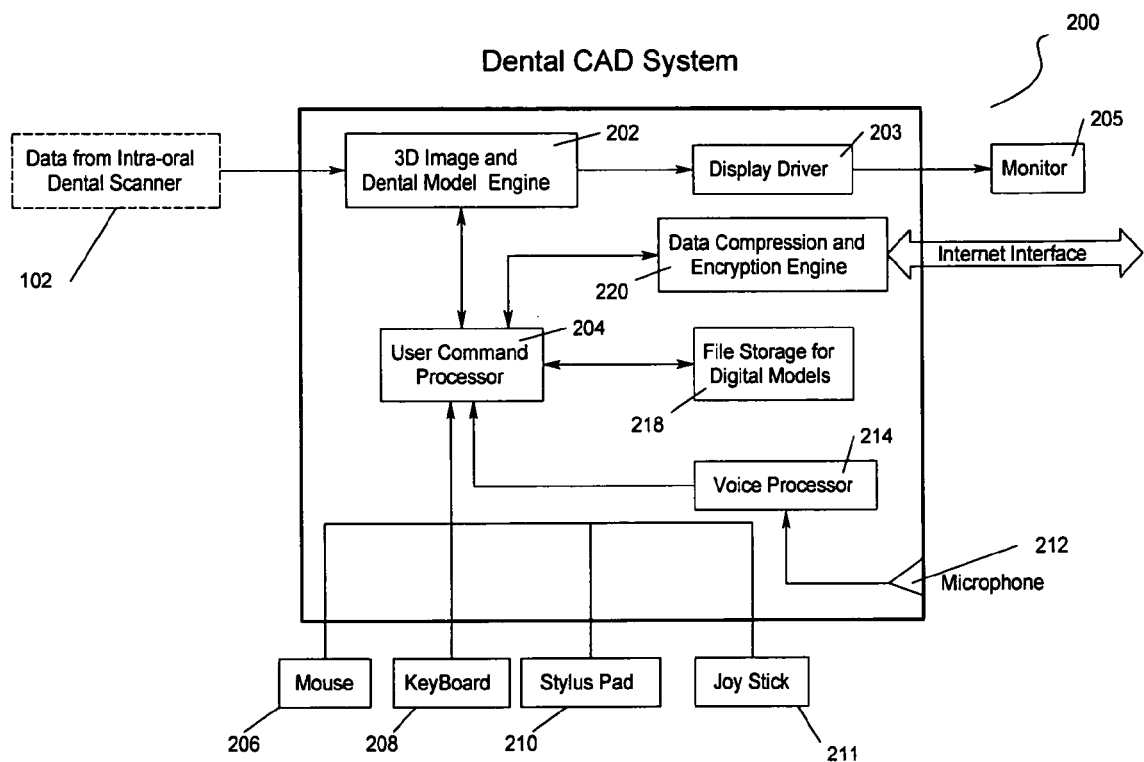
FIG. 2 shows a system and method for viewing digital dental models and performing treatment planning.

Referring now to FIG. 2, a dental CAD system 200 for viewing digital dental models and performing treatment planning is presented. Data from an intra-oral dental scanner 102 is processed by a 3D image and dental model engine 202 and displayed as a scaled 3D view of the dental structures.

The 3D image and dental model engine 202 also assesses the quality of the acquired digital dental model and can display to the user highlighted regions where the digital dental model reflects an anomalous surface contour, or where uncertainties in the calculated estimate of the surface contour exceeds a user specified limit. The output of the 3D image and dental model engine 202 is provided to a display driver 203 for driving a display or monitor 205.

The 3D image and dental model engine 202 communicates with a user command processor 204, which accepts user commands generated locally or over the Internet. The user command processor 204 receives commands from a local user through a mouse 206, a keyboard 208, or a stylus pad 210 or joystick 211. Additionally, a microphone 212 is provided to capture user voice commands or voice annotations. Sound captured by the microphone 212 is provided to a voice processor 214 for converting voice to text. The output of the voice processor 214 is provided to the user command processor 204. The user command processor 204 is connected to a data storage unit 218 for storing files associated with the digital dental models.

While viewing the 3D representation of the digital dental model, the user may use mouse 206, keyboard 208, stylus pad 210, joy stick 211 or voice inputs to control the image display parameters on the monitor 205, including, but not limited to, perspective, zoom, feature resolution, brightness and contrast. Regions of the 3D representation of the digital dental model that are highlighted by the dental CAD system as anomalous are assessed by the user and resolved as appropriate. Following the user assessment of the 3D image of the digital dental model, the dental CAD system provides the user with a data compression and encryption engine 220 to process files for secure transmission over the internet.

The dental CAD system 200 also provides the user with tools to perform a variety of treatment planning processes using the digital dental models. Such planning processes include measurement of arch length, measurement of arch width and measurement of individual tooth dimensions.

In planning for a tooth crown procedure, conventionally, a tooth isolation is prepared by cutting the tooth involved with the dental treatment out of a cast model made from an elastomer impression. A process discussed next provides an alternative process that utilizes a digital dental model and the dental CAD system 200 to prepare a 3D digital model of a tooth isolation. Using this process, an operator utilizes the CAD system 200 to isolate the tooth from the complete digital dental model and then creates a digital model of just the single tooth.

Figure 3:
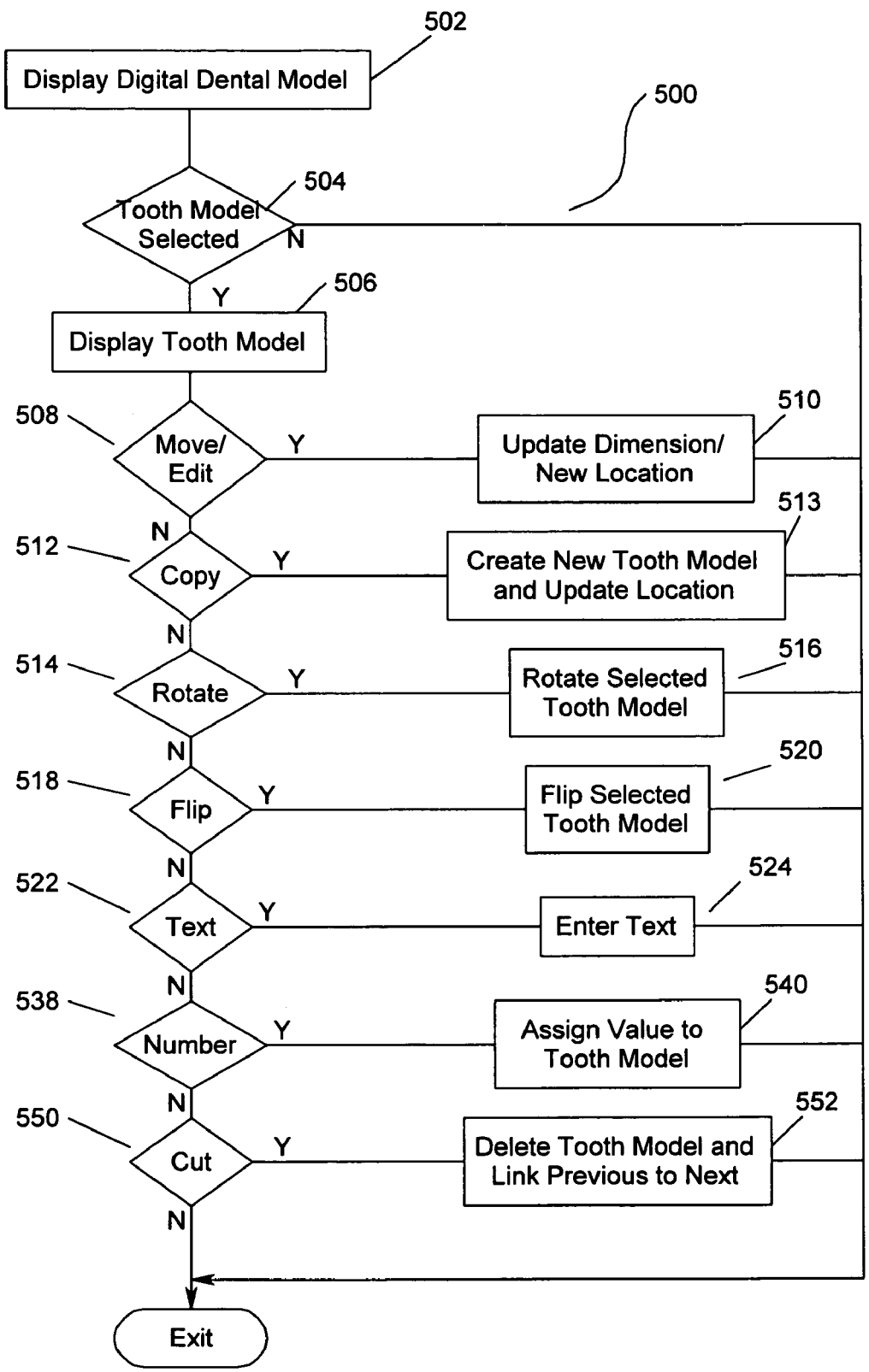
FIG. 3 shows a process to edit a digital model of a tooth.

Referring now to FIG. 3, the routine or process 500 to edit a digital dental model is disclosed in more detail. Upon entry, the digital dental model is displayed (step 502). Next, the process checks if one or more teeth in the digital dental model has been selected (step 504). If not, the routine simply exits. Alternatively, if the user has specified parameters sufficient to identify one tooth model or tooth object from the rest of the teeth, the routine highlights the tooth model (506). The parameters can be a set of points delineating one or more cutting planes separating one tooth from its neighboring teeth. Alternatively, the parameter can simply be a selection of a particular tooth model which has already been embedded with dimensional information about the tooth so that 3D data on the selected tooth can be retrieved from a file.

Next, the routine determines if the tooth model or object has been moved or digitally edited (step 508). If so, the routine updates the dimensions and key points of the tooth model, as well as the new location of the tooth model if it has been moved (step 510). Using the editing capability, the routine can be used to design a base and a mounting post or stem on the tooth model, for example. Alternatively, again using the edit capability, the routine can be used to design a base and a hole in the base for receiving a pre-fabricated mounting post or stem. After completing step 510, the routine deselects the tooth model and exits the edit routine.

If the tooth model has not been moved or stretched, the routine tests if selected tooth model(s) is/are to be copied (step 512). If so, the routine creates new tooth models or tooth object(s) based on the selected object(s) and links these new objects to existing tooth objects before exiting the routine (step 513). Alternatively, if the user does not want to copy objects, the routine checks if the user wishes to rotate selected tooth object(s) (step 514). If the objects are to be rotated, the routine complies with the request (step 516) where the selected object(s) are rotated and their new positions are noted in the linked list data structure. Afterward, the routine deselects the object(s) and exits.

From step 514, if the tooth objects are not to be rotated, the routine checks if the user wishes to flip the tooth objects (step 518). If so, the routine flips them in step 520 and updates the location of the selected objects therein before exiting the routine. Alternatively, from step 522, the user may wish to enter text associated with the selected objects. If so, the routine allows the user to enter text and to associate the text with the selected objects (step 524) by adding the text to the linked list data structure for the objects. The text entered in step 524 may include numbers as literals. After step 524, the routine deselects the object(s) and exits.

Alternatively, from step 522, the routine checks if the user has assigned a number such as the length or width of the selected tooth object(s) (step 538). If so, the routine proceeds with step 540. The number(s) entered in step 540 is/are dimensional assignments which are entered as part of the dimensions of the tooth object(s) and the size of the object(s) is/are changed. From step 540, the routine deselects the object(s) and exits.

From step 538, if numbers are not entered, the routine checks if the user wishes to cut the selected tooth object(s) (step 550). If so, the respective object(s) are deleted and the link associated with the element immediately prior to the first selected object is linked to the element immediately after the last selected tooth object (step 552). Further, the data structures associated with the deleted objects are cleaned-up such that the memory allocated to the deleted objects is released back for other uses. From step 550 and step 552, the routine deselects the object(s) and exits.

The original data structure prior to the edit operation is temporarily archived in memory to enable the operation of the "Undo" option. The "Undo" option is useful in the event that the user wishes to change his or her mind after seeing the edited tooth object(s). Voice recognition is useful for certain data entry aspects such as the entering of text annotation and the selection of components.

Figure 4:
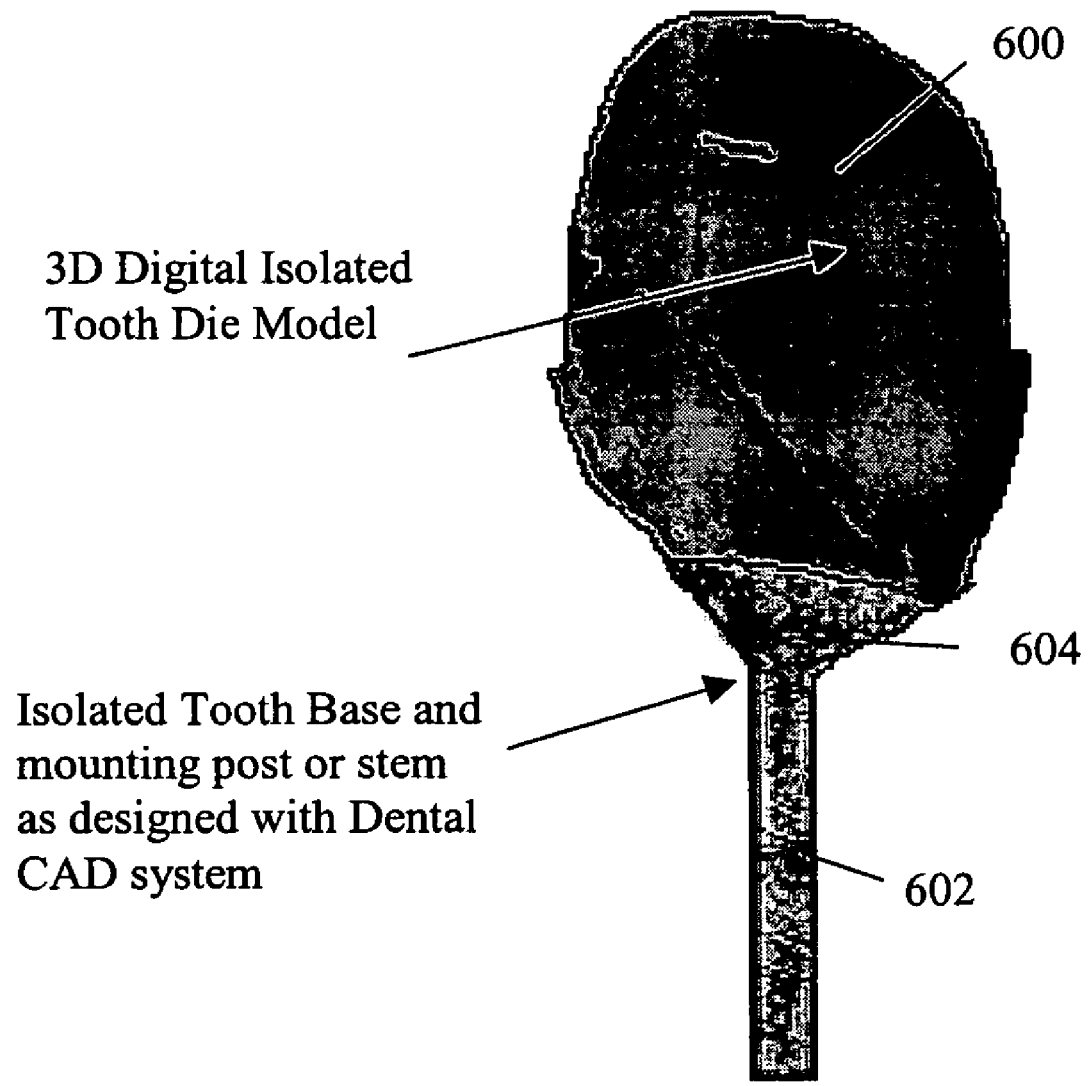
FIG. 4 illustrates an example of a digital model for an isolated tooth die with a base that includes a mounting post or stem.
Figure 5:
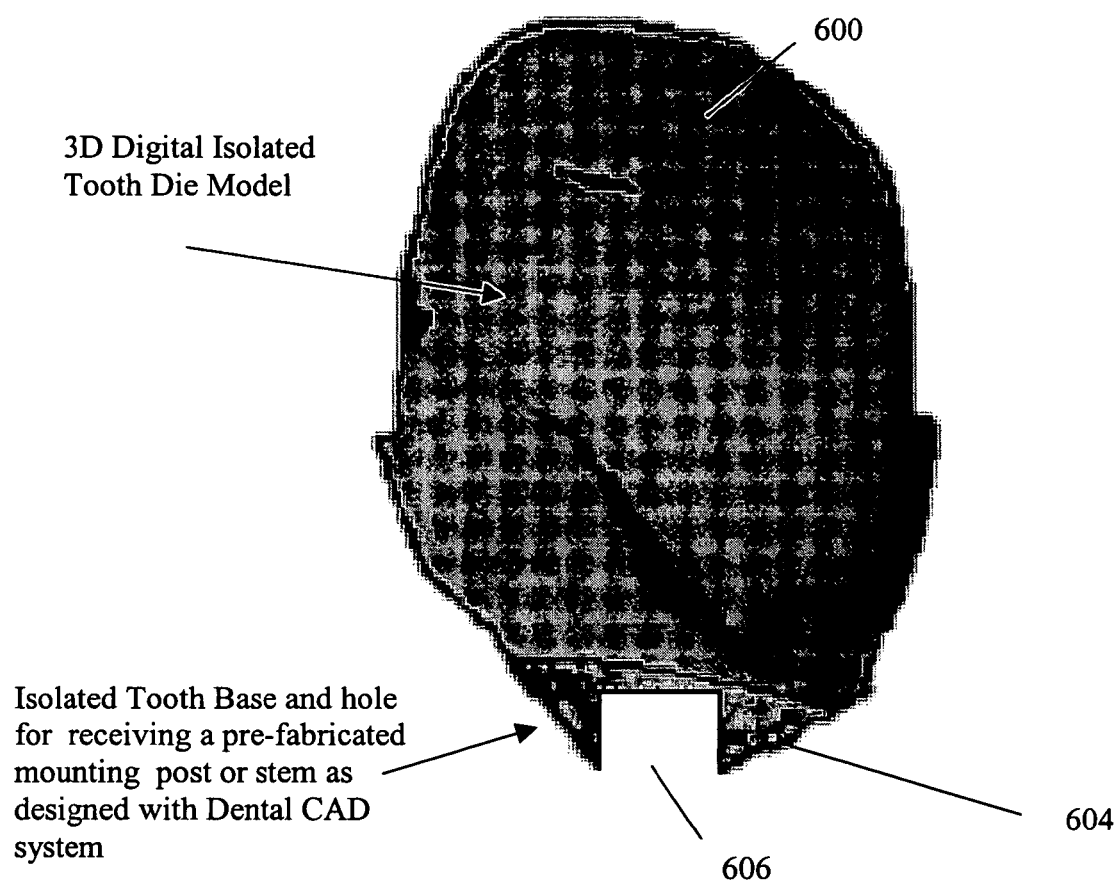
FIG. 5 illustrates an example of a digital model for an isolated tooth die with a base that includes a hole for receiving a pre-fabricated mounting post or stem.

In FIG. 4, a digital model 600 of an isolated single tooth die with a mounting post or stem attached to the tooth base is shown. The system of FIG. 2 is used to design a base 604 and a mounting post or stem 602 on the digital model 600 of the isolated tooth die. Alternately as shown in FIG. 5, the system of FIG. 2 is used to design a base 604 with a hole 606 shown in cross section for receiving a pre-fabricated mounting post or stem on the digital model 600 of the isolated tooth die. This digital model 600 with the base 604 and either 1) the mounting post or stem 602, or 2) the hole 606 in the base 604, is referred to herein as a digital isolated tooth die model. Once completed and checked by the dental technician if needed, the digital file for the digital isolated tooth die model is transferred to a CIM system where a physical model of the digital isolated tooth die model is fabricated that accurately reflects the geometry and details of the digital isolated tooth die model. The fabricated physical model of the digital isolated tooth die model will typically be used by the dental laboratory as a pattern to prepare the permanent crown for the modeled tooth.

The process described above for a single tooth crown may be extended to apply to construction of digital models for restorative dental prosthetics in general and the fabrication of physical models for any number of teeth.

While the present invention has been described in connection with certain preferred embodiments, it will be understood that it is not limited to those embodiments. On the contrary, it is intended to cover all alternatives, modifications and equivalents as may be included within the spirit and scope of the invention as defined in the appended claims.

The invention claimed is:

1. A method for treating teeth, comprising:
scanning a dental structure to generate a digital dental model, said digital dental model comprising a three dimensional representation of teeth and gingiva surface contours in a scanned dental structure;
modifying the digital dental model to isolate a tooth and create one or more digital isolated tooth die models, wherein each of said digital isolated tooth die models comprises a digital three dimensional tooth surface, a tooth base and a hole for receiving a pre-fabricated mounting post or stem dimensioned to the tooth base;
creating physical models from the digital dental model and said one or more digital isolated tooth die models using Stereo Lithographic Apparatus (SLA) equipment, where said physical models replicate the structures of the digital dental model and said one or more digital isolated tooth die models; and
using the physical models as a pattern for fabrication and fit check of a dental prosthetic.

2. The method of claim 1, further comprising utilizing a dental computer aided design system to view the digital dental model and create the one or more digital isolated tooth die models.

3. The method of claim 2, wherein creating the one or more digital isolated tooth die models includes selecting a tooth to be isolated, isolating said tooth and adding a hole to a base of the isolated tooth, and saving the digital isolated tooth die model as a unique digital file.

4. The method of claim 1, wherein the physical models contain unique identifier markings.

5. A system for treating teeth, comprising:
means for intra-orally scanning a dental structure to generate a digital dental model, said digital dental model comprising a three dimensional representation of teeth and gingiva surface contours in the scanned dental structure;
means for modifying the digital dental model to isolate a tooth and create one or more digital isolated tooth die models, wherein each of said digital isolated tooth die models comprises a digital three dimensioned tooth surface, a tooth base and a hole for receiving a pre-fabricated mounting post or stem dimensioned to the tooth base;
and means for creating physical models of the digital dental model and said one or more digital isolated tooth die models, whereby the physical models can serve as a pattern for fabrication and fit check of a dental prosthetic.

6. A system for treating teeth, comprising:
a scanner to generate a digital dental model, said digital dental model comprising a three dimensional representation of teeth and gingiva surface contours in a scanned dental structure;
a dental computer aided design system for modifying the digital dental model in designing one or more digital isolated tooth die models, wherein each of said digital isolated tooth die models comprises a digital three dimensioned tooth surface, a tooth base and a hole for receiving a pre-fabricated mounting post or stem dimensioned to the tooth base;
and a Stereo Lithographic Apparatus (SLA) system coupled to the dental computer aided design system for creating physical models from the digital dental model and said one or more digital isolated tooth die models, whereby the physical models can serve as a pattern for fabrication and fit check of a dental prosthetic.

7. The system of claim 6, wherein the dental computer aided design system is used to add an identifier marking that is evident on the physical models.

8. The system of claim 6, wherein the scanner comprises an intra-oral scanner.

9. The system of claim 6, wherein the computer aided design system creates the one or more digital isolated tooth die models by selecting a tooth to be isolated, isolating said tooth and adding a hole to a base of the isolated tooth, and saving the digital isolated tooth die model as a unique digital file.

10. The system of claim 6, wherein the physical models contain unique identifier markings.

11. The system of claim 6, comprising a CIM system coupled to the computer aided design system.

12. The system of claim 11, wherein the CIM system fabricates a physical model of the digital isolated tooth die model reflecting the geometry of the digital isolated tooth die model.

13. The system of claim 12, wherein the fabricated physical model of the digital isolated tooth die model provides a pattern to prepare a permanent crown for the modeled tooth.

14. The system of claim 13, wherein the fabricated physical model is used by a dental laboratory.

15. The system of claim 13, wherein the fabricated physical model is used by a dental technician.

16. The system of claim 13, wherein the fabricated physical model is used by a doctor.

17. The system of claim 13, wherein the fabricated physical model is used by an orthodontist or a dentist.

* * * * *